(12) United States Patent
McWethy et al.

(10) Patent No.: US 7,033,343 B2
(45) Date of Patent: *Apr. 25, 2006

(54) RETRACTABLE NEEDLE MEDICAL DEVICE FOR INJECTING FLUID FROM A PRE-FILLED CARTRIDGE

(75) Inventors: Robert T. McWethy, Ventura, CA (US); John Barker, Ventura, CA (US); Thor R. Halseth, Agoura, CA (US); Bernardo Challiol, Ventura, CA (US)

(73) Assignee: MDC Investment Holdings, Inc., Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 94 days.

(21) Appl. No.: 10/098,729

(22) Filed: Mar. 15, 2002

(65) Prior Publication Data

US 2002/0169421 A1  Nov. 14, 2002

Related U.S. Application Data

(60) Provisional application No. 60/341,431, filed on Dec. 13, 2001, provisional application No. 60/276,407, filed on Mar. 15, 2001.

(51) Int. Cl.
*A61M 31/00* (2006.01)

(52) U.S. Cl. ............... 604/506; 604/198; 604/201; 604/227; 604/232; 604/218; 222/327; 222/386

(58) Field of Classification Search ............. 604/110, 604/263, 197, 198, 192, 187, 181, 218, 227, 604/232, 234, 235, 240–243; 222/325–327, 222/386
See application file for complete search history.

(56) References Cited

U.S. PATENT DOCUMENTS

| 3,306,290 A | 2/1967 | Weltman |
| 4,585,445 A | 4/1986 | Hadtke |
| 4,655,751 A | 4/1987 | Harbaugh |
| 4,675,005 A | 6/1987 | DeLuccia |
| 4,723,943 A | 2/1988 | Spencer |
| 4,731,068 A | 3/1988 | Hesse |
| 4,737,144 A | 4/1988 | Choksi |
| 4,738,663 A | 4/1988 | Bogan |
| 4,744,790 A | 5/1988 | Jankowski et al. |
| 4,744,791 A | 5/1988 | Egolf |
| 4,767,413 A | 8/1988 | Haber et al. |
| 4,804,372 A | 2/1989 | Laico et al. |
| 4,820,275 A | 4/1989 | Haber et al. |
| 4,826,489 A | 5/1989 | Haber et al. |

(Continued)

FOREIGN PATENT DOCUMENTS

WO  00/37125  6/2000

*Primary Examiner*—Cris Rodriguez
(74) *Attorney, Agent, or Firm*—Stephen H. Eland; Dann, Dorfman, Herrell and Skillman

(57) ABSTRACT

A device for injecting fluid from a pre-filled cartridge is provided. The device includes a needle for piercing a patient. After an injection, the needle can be retracted to prevent inadvertent contact with the contaminated needle. A needle retainer releasably retains the needle in the retracted position. The needle can subsequently be re-extended to administer a subsequent injection. After the cartridge is emptied, the cartridge can be removed, if desired, and replaced with another cartridge for additional injections. Alternatively, the needle can be retracted into the device and safely disposed of in a sharps container.

28 Claims, 11 Drawing Sheets

U.S. PATENT DOCUMENTS

| | | |
|---|---|---|
| 4,834,717 A | 5/1989 | Haber et al. |
| 4,919,657 A | 4/1990 | Haber et al. |
| 4,931,040 A | 6/1990 | Haber et al. |
| 4,935,014 A | 6/1990 | Haber |
| 4,946,441 A | 8/1990 | Laderoute |
| 4,988,339 A | 1/1991 | Vadher |
| 5,067,945 A | 11/1991 | Ryan et al. |
| 5,078,698 A | 1/1992 | Stiehl et al. |
| 5,098,382 A | 3/1992 | Haber et al. |
| 5,106,379 A | 4/1992 | Leap |
| 5,112,307 A | 5/1992 | Haber et al. |
| 5,167,632 A | 12/1992 | Eid et al. |
| 5,167,641 A | 12/1992 | Schmitz |
| 5,201,708 A | 4/1993 | Martin |
| 5,201,719 A | 4/1993 | Collins et al. |
| 5,261,880 A | 11/1993 | Streck et al. |
| 5,269,766 A | 12/1993 | Haber et al. |
| 5,306,258 A | 4/1994 | de la Fuente |
| 5,330,440 A | 7/1994 | Stanners et al. |
| 5,336,200 A | 8/1994 | Streck et al. |
| 5,346,480 A | 9/1994 | Hess et al. |
| 5,350,367 A | 9/1994 | Stiehl et al. |
| 5,358,491 A | 10/1994 | Johnson et al. |
| 5,360,408 A | 11/1994 | Vaillancourt |
| 5,368,568 A | 11/1994 | Pitts et al. |
| 5,405,326 A | 4/1995 | Haber et al. |
| 5,429,611 A | 7/1995 | Rait |
| 5,445,620 A | 8/1995 | Haber et al. |
| 5,514,107 A | 5/1996 | Haber et al. |
| 5,531,706 A * | 7/1996 | de la Fuente ............... 604/198 |
| 5,573,513 A | 11/1996 | Wozencroft |
| 5,709,662 A | 1/1998 | Olive et al. |
| 5,891,104 A | 4/1999 | Shonfeld et al. |
| 5,997,512 A | 12/1999 | Shaw |
| 5,997,513 A | 12/1999 | Smith et al. |
| 6,036,675 A | 3/2000 | Thorne et al. |
| 6,752,798 B1 * | 6/2004 | McWethy et al. ........... 604/506 |
| 2001/0004970 A1 | 6/2001 | Hollister et al. |

\* cited by examiner

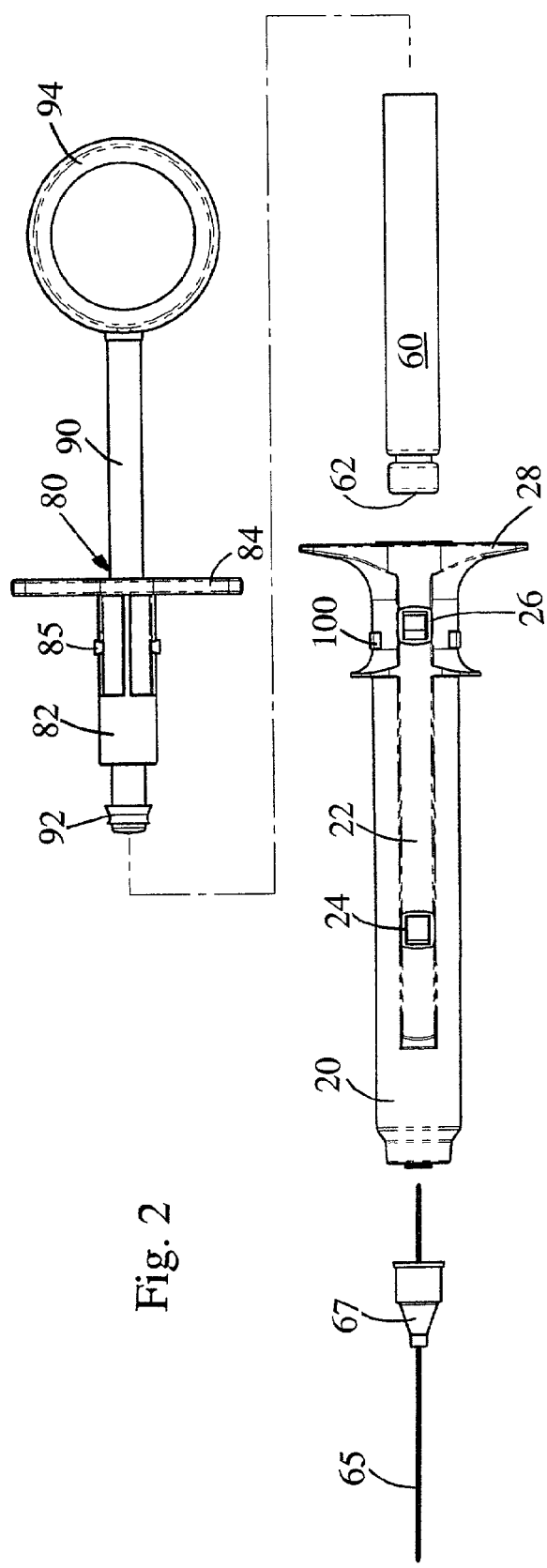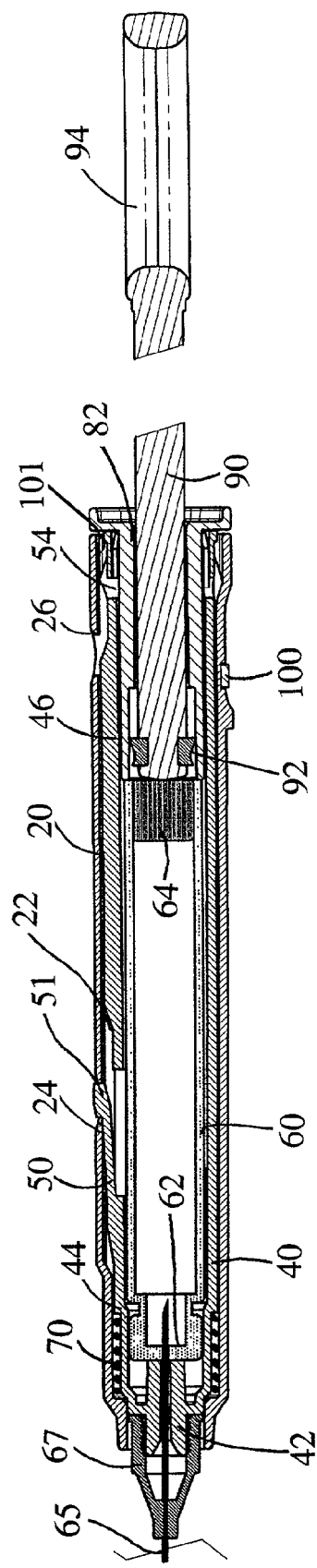
Fig. 2
Fig. 3

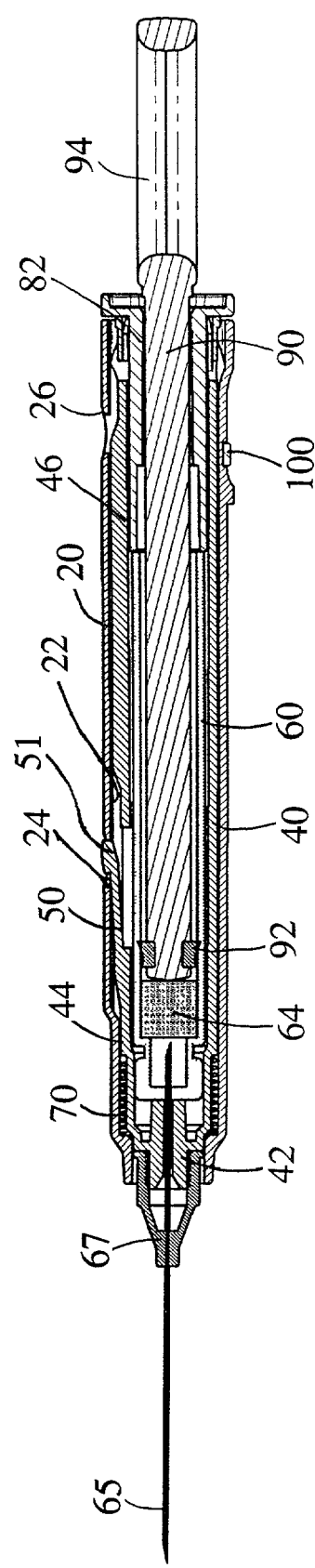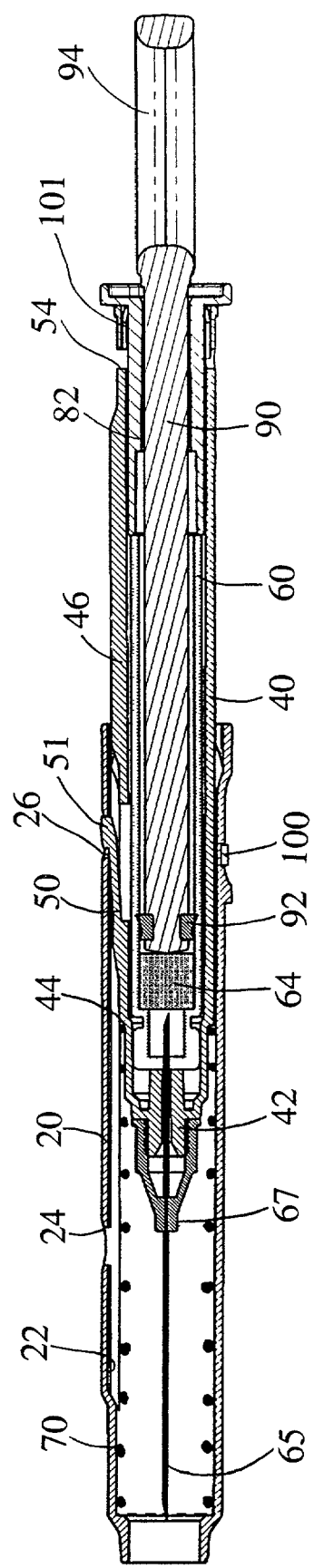
Fig. 4
Fig. 5

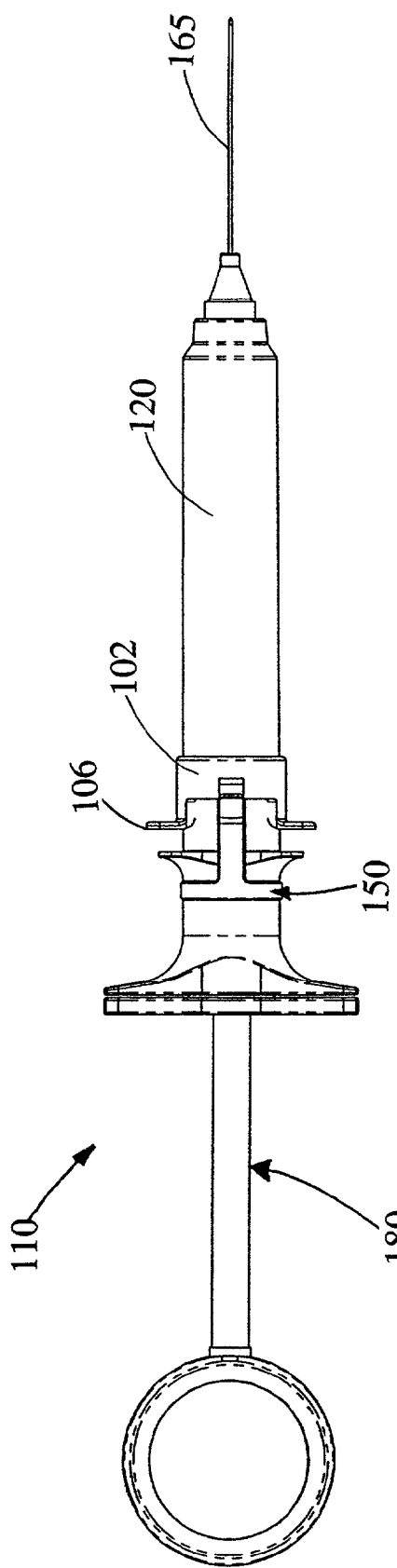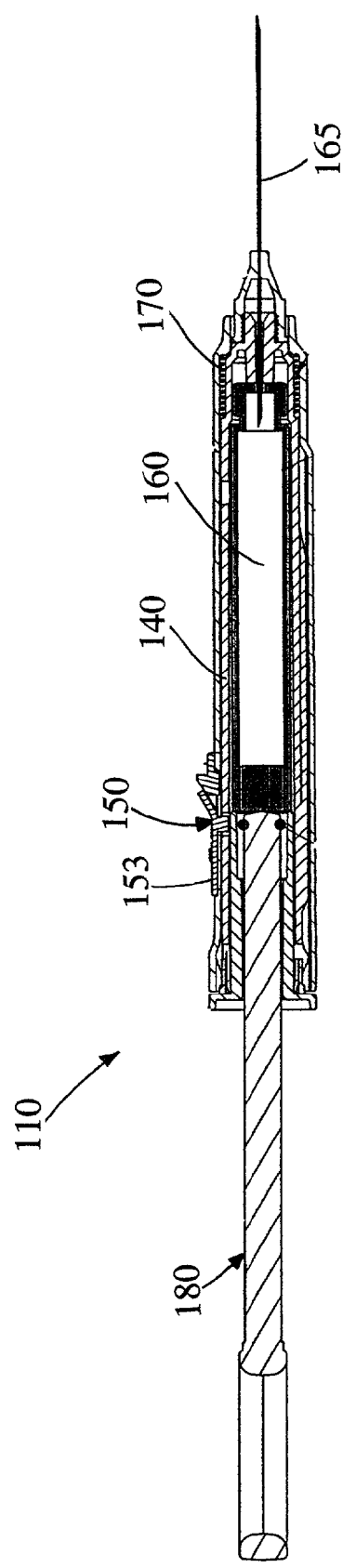
Fig. 8
Fig. 9

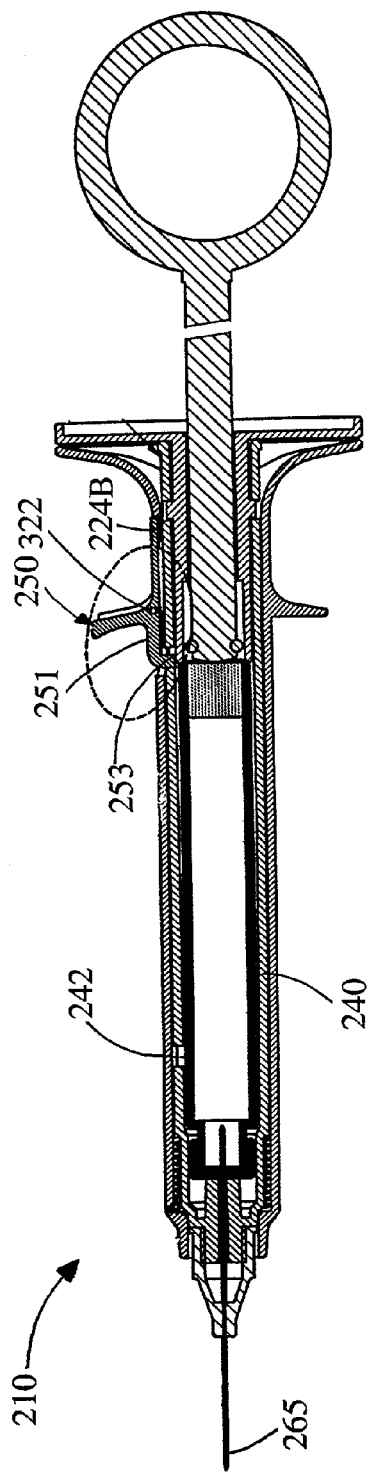
Fig. 13A
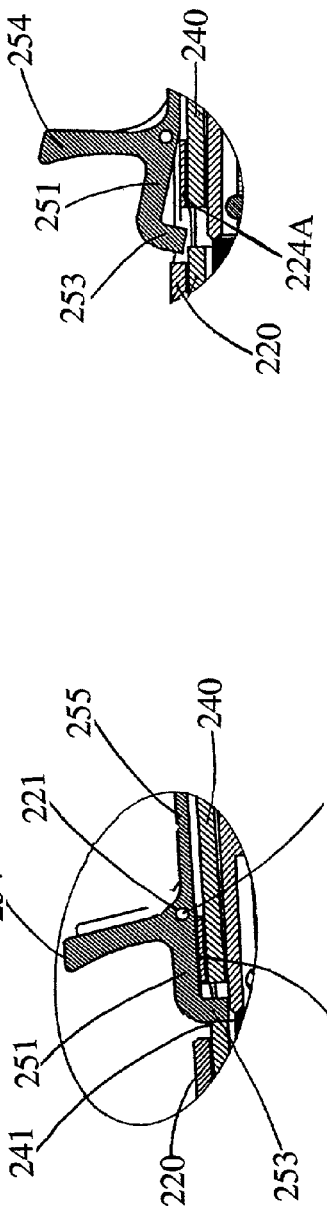
Fig. 13B
Fig. 13C

RETRACTABLE NEEDLE MEDICAL DEVICE FOR INJECTING FLUID FROM A PRE-FILLED CARTRIDGE

PRIORITY APPLICATIONS

The present application claims priority to U.S. Provisional Application No. 60/276,407 filed Mar. 15, 2001, and U.S. Provisional Application No. 60/341,431, filed Dec. 13, 2001. Each of the foregoing applications is hereby incorporated herein by reference.

FIELD OF THE INVENTION

The present invention relates to needle-bearing medical devices having a retractable needle for injecting fluid into a patient. More specifically, the present invention relates to such a device configured for injecting fluid from a pre-filled cartridge. Preferably, the needle is selectively retractable and re-extendable during use to allow the contaminated needle to be shielded between successive needle injections. In one embodiment of the invention, the needle is permanently retractable after use so that the contaminated needle is shielded to prevent inadvertent contact with the sharpened tip of the needle.

BACKGROUND

Various types of medical devices employ a needle for piercing the skin of a patient for diagnostic or therapeutic purposes. One such device is a device for introducing medicine from a pre-filled cartridge into a patient. Handling of such medical devices after the needle is withdrawn from the patient can result in transmission of various pathogens, most notably human immunodeficiency virus (HIV), due to an inadvertent needle stick to medical personnel.

Several devices are known that allow fluid to be injected into a patient from a pre-filled cartridge. For instance, in dental practice, a cartridge injector is used for injecting novocaine into a patient. These cartridge injectors are normally made with metal, that may be chrome or nickel plated and are intended to be sterilized by an autoclave after use.

When using a dental injector, it is common to administer several small doses of novocaine. After the first injection, the needle is considered contaminated, and current practice, as outlined by OSHA guidelines, requires recapping the needle. Although recapping by hand is prohibited by OSHA guidelines, some dentists still practice this unsafe technique, which can lead to an inadvertent needle stick. One recommended technique for safely recapping the needle uses a cap holder, mounted to the dental tray being used. Although safer than recapping the needle by hand, using a cap holder still exposes the contaminated needle when the device is moved from the patient's mouth to the cap holder for recapping. Another problem with recapping is that if the dentist is not careful when centering the needle into the cap, the needle tip can scrape the sidewall of the cap. If this happens, the needle can be dulled or can scrape off small pieces of plastic that could be injected into the patient during subsequent injections.

SUMMARY OF THE INVENTION

In light of the foregoing, a medical device is provided that allows a series of injections to be made to a patient. Between each injection, the contaminated needle is shielded against inadvertent contact. After use, the needle is shielded to prevent inadvertent contact with the contaminated needle during subsequent handling of the used device.

More specifically, the present invention provides a medical device having a hollow housing for receiving a pre-filled cartridge and a plunger for expelling fluid from the cartridge. A needle having a sharpened tip projects forwardly from the forward end of the housing. A biasing element, such as a spring, is operable to displace the needle rearwardly. A first lock releasably locks the needle in a projecting position in which the sharpened tip of the needle is exposed for use. A second lock releasably retains the needle in a shielded position in which the sharpened tip of the needle is shielded against inadvertent contact.

The present invention also provides methods for safely providing a plurality of injections to a patient from a medical device having a needle with a sharpened tip operable between a projecting position, in which the needle is exposed for use, and a retracted position, in which the needle is shielded against inadvertent contact. According to the method, the patient is pierced with the sharpened tip of the needle, and fluid contained in a cartridge is injected into the patient. The needle is then retracted to a first retracted position so that the sharpened needle tip is shielded against inadvertent contact. The needle is releasably locked in the first retracted position by a first lock. The needle is then re-extended into the projecting position, the patient is pierced a second time, and fluid is injected into the patient a second time. In one method, the cartridge can be removed and a new cartridge inserted to provide additional medication for further injections.

DESCRIPTION OF THE DRAWINGS

The foregoing summary as well as the detailed description below will be better understood when read in conjunction with the drawings, in which:

FIG. 2 is an exploded side view of the medical device illustrated in FIG. 1;

FIG. 3 is a cross-sectional view of the medical device illustrated in FIG. 2 illustrating the device prior to injection;

FIG. 4 is a cross-sectional view of the medical device illustrated in FIG. 3, illustrating the device at the end of an injection;

FIG. 5 is a cross-sectional view of the medical device illustrated in FIG. 4, illustrating the device in a retracted position.

FIG. 8 is a side elevational view of the medical device illustrated in FIG. 7;

FIG. 9 is a cross-sectional view of the medical device illustrated in FIG. 8;

FIG. 13A is a cross-sectional view of the medical device illustrated in FIG. 12;

FIG. 13B is an enlarged fragmentary cross-sectional view of an actuator of the medical device illustrated in FIG. 13A;

FIG. 13C is an enlarged fragmentary cross-sectional view of the actuator of the medical device illustrated in FIG. 13B, showing the actuator in an actuated position;

DETAILED DESCRIPTION OF THE PREFERRED EMBODIMENTS

Figure 1:
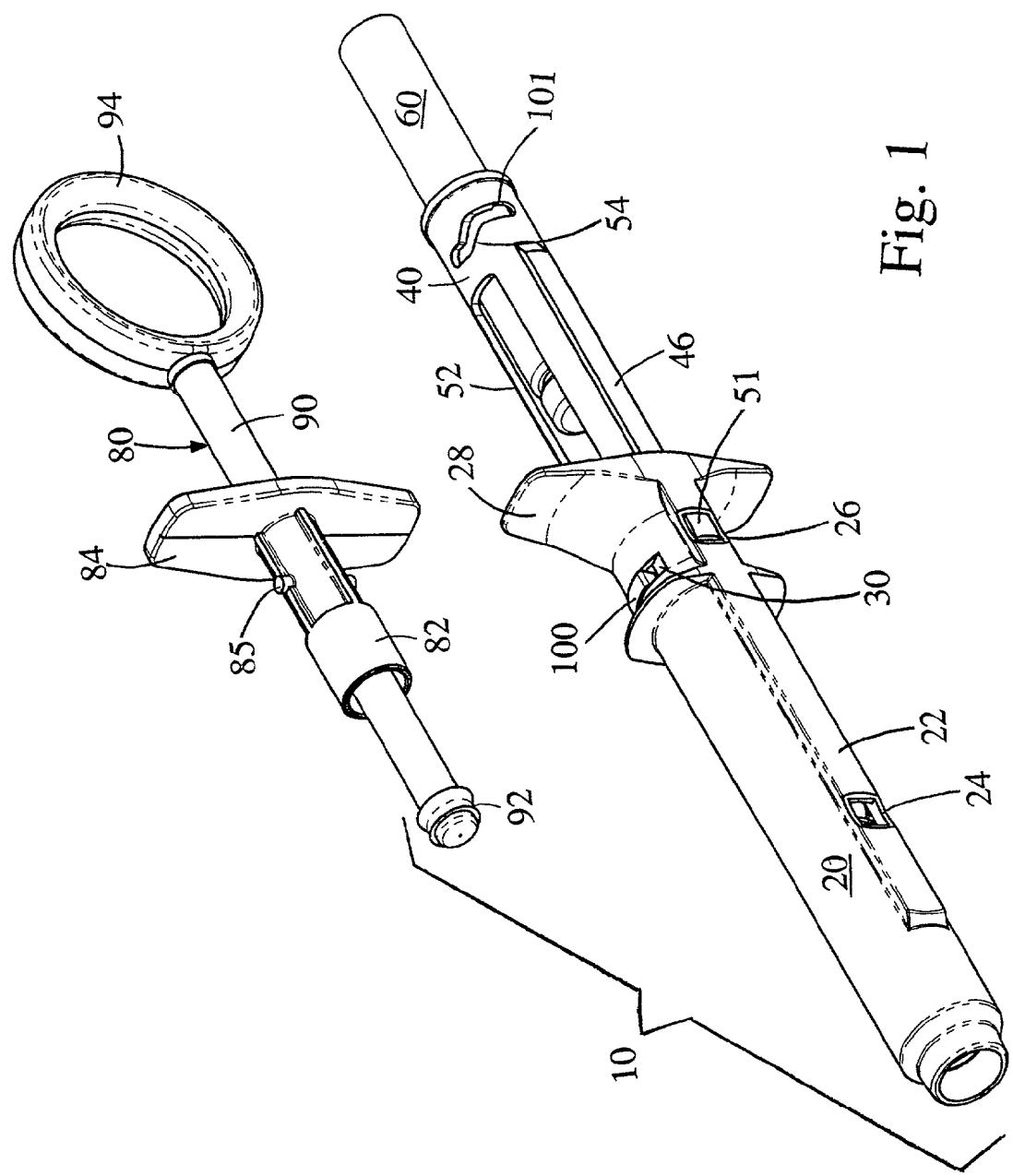
FIG. 1 is a perspective view a retractable needle medical device with a plunger assembly detached.

Referring now to the figures in general, and FIGS. 1–5 specifically, a medical device is designated generally 10. The device 10 includes a needle 65 for piercing a patient, and a plunger assembly 80 for ejecting medication from a pre-filled cartridge 60 into a patient. At the end of an injection, the needle 65 can be automatically shielded to prevent inadvertent contact with the contaminated needle. Subsequently, the needle can be re-extended to provide a further injection to the patient. In this way, a plurality of injections can be given to a patient while allowing the needle to be safely shielded between injections.

The device includes a generally cylindrical barrel 20 and an inner housing 40 that is displaceable within the barrel 20. The inner housing 40 is generally hollow, having a socket for receiving the cartridge 60. The needle 65 is attached to the forward end of the inner housing 40, as shown in FIG. 3. A plunger assembly 80 attached to the rearward end of the inner housing 40 is operable to expel the medicine from the cartridge.

A compression spring 70 is disposed between the barrel 20 and the inner housing 40. The spring 70 biases the inner housing 40 rearwardly toward a retracted position in which the needle 65 is shielded within the barrel as shown in FIG. 5. A latch 50 attached to the inner housing 40 engages the barrel 20 to releasably retain the inner housing against the bias of the spring, as shown in FIG. 4.

The latch 50 includes a manually actuable button 51. By depressing the button 51, the latch 50 disengages the barrel 20 so that the inner housing 40 and attached needle 65 can be retracted. In the retracted position the latch 50 re-engages the barrel 20, as shown in a FIG. 5. By depressing the button 51 and pushing the plunger assembly 80 forwardly, the inner housing 40 and attached needle 65 can be re-extended until the latch 50 re-engages the barrel in the forward position, as shown in FIG. 4.

Referring now to FIGS. 1–3, the details of the injector 10 will be described in greater detail. The outer barrel 20 is generally cylindrical, having an open forward end and an open rearward end. An annular shoulder formed in the interior of the barrel adjacent the open front end provides a surface that the spring 70 bears against. The barrel 20 comprises a pair of opposing finger grips 28 projecting radially outwardly from the rearward end of the barrel. The finger grips provide a manual surface for grasping the barrel during use.

An axially elongated recess or channel 22 is formed in the barrel such that the channel protrudes radially outwardly from the side of the barrel, as shown in FIGS. 1 and 3. The channel 22 preferably extends substantially the length of the barrel 20 from the rearward end of the barrel, terminating short of the forward end of the barrel. The channel 22 provides a clearance space for the latch 50 during axial displacement of the inner housing 40 relative to the barrel 20. In addition, the channel 22 cooperates with an elongated alignment rib 46 formed on the inner housing 40 to prevent rotation of the inner housing relative to the barrel 20.

The barrel 20 includes a pair of locking windows 24, 26 that cooperate with the latch 50 of the inner housing to releasably latch the inner housing 40 to the barrel 20. The locking windows 24, 26 are axially aligned and spaced apart from one another, as shown in FIG. 2. Preferably, the locking windows 24, 26 are disposed along the length of the channel 22. The latch 50 on the inner housing 40 cooperates with the front window 24 to releasably lock the inner housing in a forward position, and the latch cooperates with the rear window 26 to releasably lock the inner housing in a retracted position.

Referring to FIG. 1, a pair of lateral slots 30 are formed in the wall of the barrel 20 transverse the axis of the barrel, adjacent the rearward end of the barrel. Preferably the slots 30 are formed approximately 80 degrees apart from one another to provide a top slot and a bottom slot through the wall of the barrel. The slots 30 cooperate with a locking clip 100 to prevent the inner housing 40 from being completely removed from the barrel 20, as discussed further below.

Referring now to FIGS. 1 and 3, the inner housing 40 comprises an elongated hollow cylinder. The front end of the inner housing is generally closed, having a nose 42 that cooperates with a needle hub 67 to attach the needle to the inner housing. Specifically, the needle 65 is fixedly attached to a needle hub 67 having a generally open rearward end forming a female connector. As shown in FIGS. 2 and 3, the needle hub 67 is mounted on the needle 65 along the length of the needle so that the forward sharpened tip of the needle projects forwardly from the needle hub and the sharpened rearward end of the needle projects rearwardly from the needle hub. As shown in FIG. 3, the nose 42 of the inner housing 40 forms a male connector that cooperates with the interior of the needle hub 67 to form a fluid-tight connection between the needle, and the inner housing. The nose 42 has a reduced diameter opening through which the rearward end of the needle 65 extends, and the length of the needle 65 projecting rearwardly from the needle hub 67 is sufficiently long to ensure that the rearward sharpened end of the needle projects into the interior of the inner housing 40 to enable the needle to pierce the septum 62 of the cartridge 60.

A circumferential shoulder 44 is formed on the exterior of the inner housing 40, adjacent the nose 42. The shoulder 44 provides a surface against which the rearward end of the spring 70 bears. In this way, an annular spring housing is formed in the radial space between the outer surface of the inner housing and the inner surface of the barrel 20, extending between the annular shoulder formed at the front and of the barrel end the circumferential shoulder 44 formed on the inner housing.

As shown in FIG. 3, the latch 50 is integrally formed in the side of the inner housing 40. The latch 50 is an axially elongated radially deformable arm biased radially outwardly toward the barrel 20. Preferably, the latch 50 has a width that is slightly less than the width of the channel 22 formed in the side of the barrel 20, so that the latch can slide freely through the channel during retraction and re-extension of the needle, as discussed further below.

A button 51 or locking tab is formed on the terminal end of the latch 50 remote from the inner housing. As shown in FIG. 3, the button 51 engages the front locking window 24 to releasably lock the inner housing against axial displacement relative to the barrel 20. Similarly, the button 51 engages the rear locking window 26 to releasably lock the inner housing against axial displacement relative to the barrel 20. A cut-out in the inner housing 40 adjacent the latch 50 provides a clearance space to allow the latch to be displaced radially inwardly out of engagement with the barrel.

Preferably, an axially elongated alignment rib 46 is formed on the exterior of the inner housing 40. As shown in FIG. 2, preferably the rib 146 is axially aligned with the latch 50. Referring again to FIG. 3, the rib 46 projects radially outwardly from the inner housing 40 into engagement with the channel 22 in the barrel 20. Preferably, the rib 46 has a width that is slightly less than the width of the channel 22 formed in the side of the barrel 20. In this way, the rib 46 forms a sliding engagement with the channel 22, allowing the inner housing 40 to slide freely axially relative to the barrel.

The engagement between the rib 46 and channel 22 operates similar to a key and keyway to prevent rotation of the inner housing relative to the barrel. In addition, the rib 46 also operates to support torque applied to the inner housing, which might otherwise be transferred to the latch 50, which could potentially fracture the latch. Such torque may be applied when the needle is screwed onto the inner housing 40, or when the plunger assembly is twisted to engage the housing.

Figure 6:
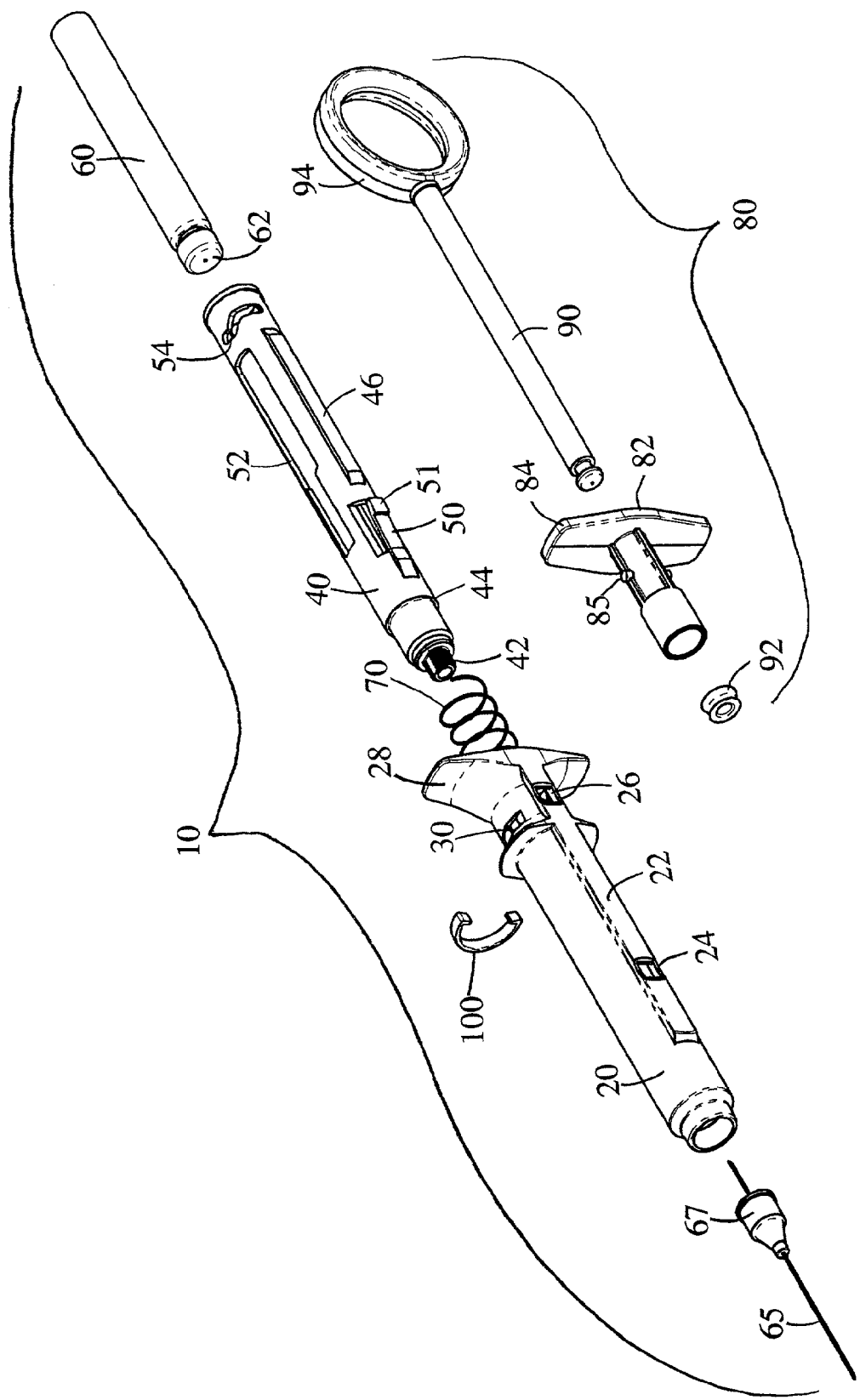
FIG. 6 is an exploded perspective view of the medical device illustrated in FIG. 1.

As shown in FIGS. 1 and 6, a pair of locking slots 54 are formed adjacent the rearward end of the inner housing. Preferably, the locking slots are modified Z-shaped slots that cooperate with locking pins 85 on the plunger assembly 80 to attach the plunger assembly to the inner housing.

The rearward end of the inner housing 40 is open, having an inner diameter that is greater than the outer diameter of the cartridge 60. In this way, the cartridge 60 can be inserted into the rearward end of the inner housing to mount the cartridge within the housing. The cartridge 60 is inserted into the inner housing until the forward end of the cartridge abuts the forward end of the inner housing so that the needle 65 pierces the cartridge, as shown in FIG. 3.

The cartridge 60 is an elongated hollow cylinder forming a fluid reservoir. The cartridge is filled with a pre-measured amount of medicinal fluid. The forward end of the cartridge 60 is sealed by a pierceable septum 62. A circumferential groove is formed on the exterior of the cartridge 60 rearward of the septum 62. The rearward end of the cartridge 60 is sealed by a piston 64 that forms a fluid-tight seal with the interior of the cartridge. The piston is axially displaceable within the cartridge to expel medicine from the cartridge.

Referring to FIGS. 1, 2 and 6, the details of the plunger assembly 80 will now be described. The plunger assembly 80 is operable to expel the medicine from the cartridge 60 during an injection. The plunger assembly 80 may be designed either as a single-use element or as a reusable element. Specifically, the plunger assembly 80 may be formed of an inexpensive readily formable material such as plastic, and permanently attached to the inner housing 40 so that the plunger assembly is discarded along with the device after use. Alternatively, the plunger assembly 80 may be formed of a durable material that can be sterilized after use. For instance, the plunger assembly may be formed of a material such as nickel-plated metal or stainless-steel that can be sterilized by an autoclave after use. If the plunger assembly is intended for reuse, the connection between the plunger assembly and the inner housing is releasable, so that the barrel 20, inner housing 40 and needle 65 can be detached and safely disposed of after use.

The plunger assembly 80 includes an elongated plunger rod 90 that is axially displaceable within the plunger sleeve 82. Preferably, a loop 94 is formed on the rear end of the plunger rod 90, forming an opening for the user's thumb to manipulate the plunger rod during use. The loop 94 and the finger grips in front of flanges 28 allow the operator to aspirate the device with one hand. In addition, preferably a circumferential groove is formed in the plunger rod 90 adjacent the front end of the plunger rod, as shown in FIG. 6. The groove provides a seat for receiving a plunger seal 92 as shown in FIG. 3.

The plunger sleeve 82 is a generally hollow cylindrical sleeve having an internal bore for receiving the plunger rod 90. A pair of finger grips 84 project radially outwardly from the rearward end of the plunger sleeve 82, providing a surface for engaging the sleeve to drive the entire plunger assembly forwardly during re-extension of the needle 65, as described below. The bore of the plunger sleeve 82 is enlarged adjacent the forward end of the sleeve so that the plunger seal 92 can be received within the forward end of the sleeve, as shown in FIG. 3. The plunger seal 92 preferably forms a fluid-tight seal with the inner wall of the cartridge.

Referring to FIGS. 1 and 6, a pair of locking pins 85 project radially outwardly from the plunger sleeve 82. Preferably, the locking pins are circumferentially spaced apart from one another approximately 80 degrees. A pair of internal channels 101 are disposed in the interior of inner housing 40 adjacent to receive locking pins 85 on plunger assembly 80 and guide the locking pins into the Z-shaped locking slots 54 as the plunger assembly is inserted into the inner housing. The locking pins 85 snap into recesses at the end of the slots to releasably connect the plunger assembly 80 to the inner housing 40.

The plunger assembly 80 is attached to the inner housing 40 as follows. After a cartridge 60 is inserted into the inner housing 40, the plunger rod 90 is withdrawn so that the front end of the plunger rod is disposed within the bore of the plunger sleeve 82, as shown in FIG. 3. The plunger assembly is inserted into the rearward end of the inner housing 40 with the locking pins 85 axially aligned with interior channels 101. The plunger assembly 80 is then advanced toward the front of the inner housing 40 until locking pins 85 enter locking slots 54. Preferably, the axial distance between the locking pins 85 and the finger grips 84 is substantially similar to the axial distance between the rearward edge of the inner housing 40 and the locking slots 54. In this way, the locking pins 85 can be readily aligned with the locking slots 54 by inserting the plunger sleeve 82 into the inner housing 40 until the finger grips 84 engage the rearward end of the inner housing.

With reference to FIG. 1, the plunger assembly 80 is rotated approximately 90 degrees relative to the view in FIG. 1 when the plunger assembly is inserted into the inner housing 40. After the locking pins 85 pass through interior channels 101 and enter locking slots 54, the plunger sleeve 82 is rotated approximately 90 degrees to lock the plunger assembly to the inner housing. This rotated orientation is reflected in the illustration in FIG. 1.

As described above, the inner housing 40 is axially displaceable relative to the barrel 20. Since the needle 65 is attached to the inner housing 40, the contaminated needle will be exposed if the inner housing is removed from the barrel after use. Accordingly, as mentioned previously, preferably the device 10 includes an element for preventing the inner housing 40 from being completely removed from the barrel 20. Specifically, preferably the device includes a locking clip 100 that provides a stop limiting the rearward displacement of the inner housing.

As shown in FIG. 6, the locking clip 100 is a generally C-shaped clip. The ends of the clip terminate in hooks that project radially inwardly. The locking clip 100 snaps onto the barrel 20 so that the terminal ends of the locking clip project radially inwardly through the side slots 30 adjacent the rearward end of the barrel. Preferably, the locking clip is attached to the barrel during manufacturing after the inner housing 40 and spring 70 are inserted into the barrel 20.

As shown in FIG. 6, a pair of opposing axially elongated access windows 52 are formed in the inner housing circumferentially spaced from the alignment rib 46. The forward end of the access windows 52 form shoulders that engage the ends of the locking clip 100 that extend into the barrel. In this way, the engagement between the locking clip 100 and the forward end of the access windows 52 limits the rearward displacement of the inner housing 40 relative to the barrel 20, thereby preventing the inner housing from being completely removed from the barrel, which would expose the contaminated needle 65.

The operation of the device will now be described. A cartridge 60 is inserted into the inner housing 40. The plunger assembly 80 is then inserted into the inner housing 40 and advanced forwardly until the locking pins 85 register with the locking slots 54 on the inner housing. The plunger sleeve 82 is then rotated so that the locking pins 85 follow the locking slots 54 until the plunger assembly is attached to the inner housing. The needle hub 67 is then attached to the forward end of the inner housing so that the rearward end of the needle 65 pierces the septum 62 on the cartridge. The septum 62 then forms a seal around the needle 65 to prevent medicine from leaking out of the cartridge 60 around the needle. Preferably, prior to attaching the plunger assembly 80 to the inner housing 40, the plunger rod 90 is displaced so that the front end of the plunger rod is disposed within the bore of the plunger sleeve 82 adjacent the front end of the plunger sleeve as shown in FIG. 3.

FIG. 3 illustrates the device 10 as it appears after the plunger assembly 80 is attached to the inner housing 40 and prior to an injection. The needle 65 is inserted into a patient. It may be desirable to check to see whether the needle pierced a blood vessel in the patient. This can be done by pulling the plunger rod 90 rearwardly. Prior to piercing the patient, the plunger rod 90 may be advanced into the cartridge a short distance until the plunger seal 92 enters the cartridge. Since the plunger seal 92 forms a fluid-tight seal with the interior of the cartridge 60, pulling rearwardly on the plunger rod forms a vacuum that displaces the cartridge piston 64 rearwardly. If the needle pierced a blood vessel in the patient, a flash of blood will enter the cartridge when the piston 64 is displaced rearwardly. Preferably the cartridge, inner housing and barrel are formed of translucent or transparent materials so that the flash of blood is visible. If blood is detected, an alternate injection can be located.

Once the needle 65 is properly inserted into the patient, the plunger rod 90 is advanced, thereby advancing the piston 64 to expel medication from the cartridge into the patient through the needle 65. To do so, the user grasps the finger grips 28 on the barrel 20 between two fingers and inserts a thumb into the loop 94, and squeezes the thumb and fingers together.

In many applications, it is desirable to inject the medication using a series of small injections. In such applications, less than the entire amount of the medication in the cartridge is injected during a single injection. After each injection, the needle 65 can be retracted to shield the needle to prevent inadvertent contact with the contaminated needle between injections.

The needle 65 is retracted as follows. The user pushes the button 51 downwardly out of engagement with the front locking window 24. The inner housing 40 is then free to be displaced rearwardly under the bias of the spring 70. However, the needle will not retract until the user releases the plunger assembly 80, which is also displaced rearwardly during retraction. Alternatively, the user can release the finger grips 28 on the barrel 20, allowing the barrel 20 to be displaced forwardly to shield the needle. Either way, the button should be pushed while the plunger assembly or barrel is released. Otherwise, the button may re-engage the front locking window before it is released.

As the inner housing 40 is displaced rearwardly relative to the barrel 20, the latch 50 is compressed radially inwardly, engaging the channel 22. In addition, during retraction, the alignment rib 46 and the button 51 ride within the channel 22, maintaining the alignment between the button and the locking windows 24, 26. At the end of retraction, the button 51 is aligned with the rear locking window 26, and the latch 50 resiliently deflects outwardly so that the button engages the rear locking window, as shown in FIG. 5. In this position, the contaminated sharpened tip of the needle is shielded within the barrel 20.

Further injections can be administered by re-extending the needle 65. This is done by pressing the button 51 downwardly out of engagement with the rear locking window 26 and simultaneously pushing the plunger assembly 80 forwardly until the button 51 is aligned with the front locking window 26. The latch 50 then resiliently deflects outwardly so that the button engages the front locking window 24. If the inner housing is advanced by pushing forward on the plunger rod, the force may also advance the piston 64, which would inadvertently expel medication from the cartridge. Accordingly, preferably the plunger assembly is advanced by grasping the finger grips 28 on the barrel and the finger grips 84 on the plunger assembly. The needle can then be re-extended without expelling medicine by pushing forward on the finger grips 84 attached to the plunger assembly.

If all of the medication is expelled from the cartridge, and further injections are desired, the empty cartridge can be replaced with a new cartridge. To do so, the needle 65 is retracted, as shown in FIG. 5, so that the inner housing 40 projects rearwardly from the barrel 20. The plunger rod 90 is then pulled rearwardly out of the cartridge 60 and into the bore of the plunger sleeve 82. Referring to FIG. 1, when the inner housing is retracted, the access windows 52 in the inner housing provide access to the cartridge. Specifically, the access windows 52 are wide enough to allow the user to grasp the cartridge to pull the cartridge out the rearward end of the inner housing. Accordingly, the cartridge is manually grasped through the access windows 52, pulled rearwardly out of engagement with the rearward end of the needle 65, and out the rearward end of the inner housing 40. A new cartridge can then be inserted through the rearward end of the inner housing and advanced until the reward end of the needle pierces the septum on the cartridge. The inner housing 40 can then be re-extended as described previously to administer further injections of medicine. In this way, a plurality of injections can be administered from a plurality of cartridges using a single device, while shielding the contaminated needle between injections.

It may be desirable to further include another lock for permanently locking the needle 65 in the retracted position after use. For instance, the barrel may include a locking recess adjacent the rearward end of the barrel, circumferentially spaced from the rear locking window 26. After the final injection is administered, the inner housing 40 is retracted rearwardly until the latch 50 engages the rear locking window 26. To permanently lock the inner housing, the button 51 is then pushed inwardly and the inner housing is rotated relative to the outer housing until the latch 50 engages the locking recess. To facilitate this twisting at the end of retraction, it may be necessary to modify the alignment rib 46 to allow the inner housing to rotate relative to the barrel after retraction.

In some instances, it is desirable to administer injections with one hand, so that the other hand can be utilized for other tasks. Referring now to FIGS. 7–11, a second embodiment of the present invention is shown and designated 110. The device 110 includes a releasable locking mechanism that may be operated with the same hand that holds the device during injections. Device 110 includes many of the same components discussed with regard to the first embodiment. This second embodiment utilizes a modified locking and unlocking mechanism using a sliding collar to actuate retraction rather than a push button.

In particular, the device 110 includes a needle 165 for piercing a patient, and a plunger assembly 180 for ejecting medication from a pre-filled cartridge 160 into a patient. The device 110 is configured for operation with one hand supporting the device. At the end of an injection, the needle 165 can be automatically shielded by actuating a release mechanism which is reachable with the hand that holds the device 110. The needle 165 can be subsequently re-extended using the same hand to provide a further injection to a patient.

The device includes a generally cylindrical barrel 120 and an inner housing 140 that is displaceable within the barrel. The barrel 120 includes a pair of opposing finger grips 128 projecting radially outwardly from the rearward end of the barrel. The finger grips provide a manual surface for grasping the barrel during use. The inner housing 140 is generally hollow, having a socket for receiving the cartridge 160. The needle 165 is attached to the forward end of the inner housing 140, as shown in FIG. 9. A plunger assembly 180 attached to the rearward end of the inner housing 140 is operable to expel the medicine from the cartridge.

Figure 11:
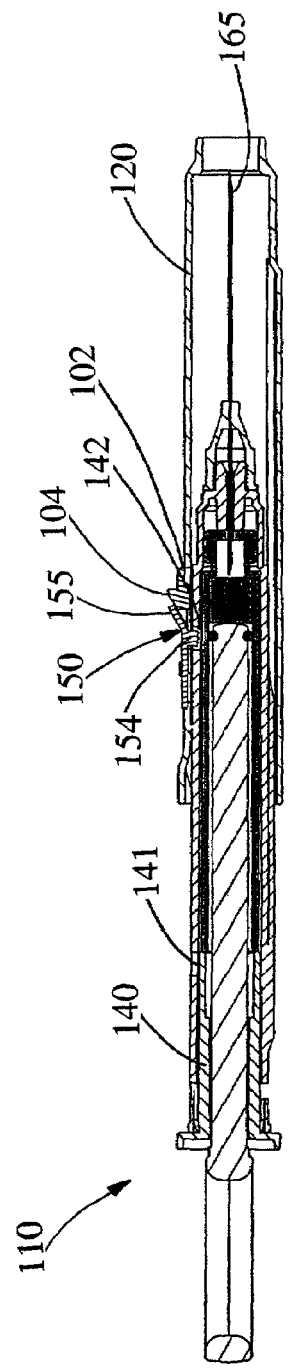
FIG. 11 is a cross-sectional view of the medical device illustrated in FIG. 7, illustrating the device after retraction.

A compression spring 170 is disposed between the barrel 120 and the inner housing 140. The spring 170 biases the inner housing 140 rearwardly toward a retracted position in which the needle 165 is shielded within the barrel, as shown in FIG. 11. A clip 150 releasably retains the inner housing 140 in a forward position against the bias of the spring 170, so that the needle 165 projects forwardly from the open forward end of the barrel.

The clip 150 includes an arcuate or C-shaped body 151 having a pair of terminal ends. A radial tab 152 extends inwardly from each terminal end on the clip 150. In addition, an elongated central cantilever beam 153 extends from the body 151. The cantilever beam 153 has a locking tab 154 that extends from an end of the beam. The clip 150 is configured to securely engage the cylindrical exterior contour of the barrel 120. When the clip 150 is mounted on the barrel 120, radial tabs 152 and locking tabs 154 are oriented towards the interior of the barrel.

Figure 7:
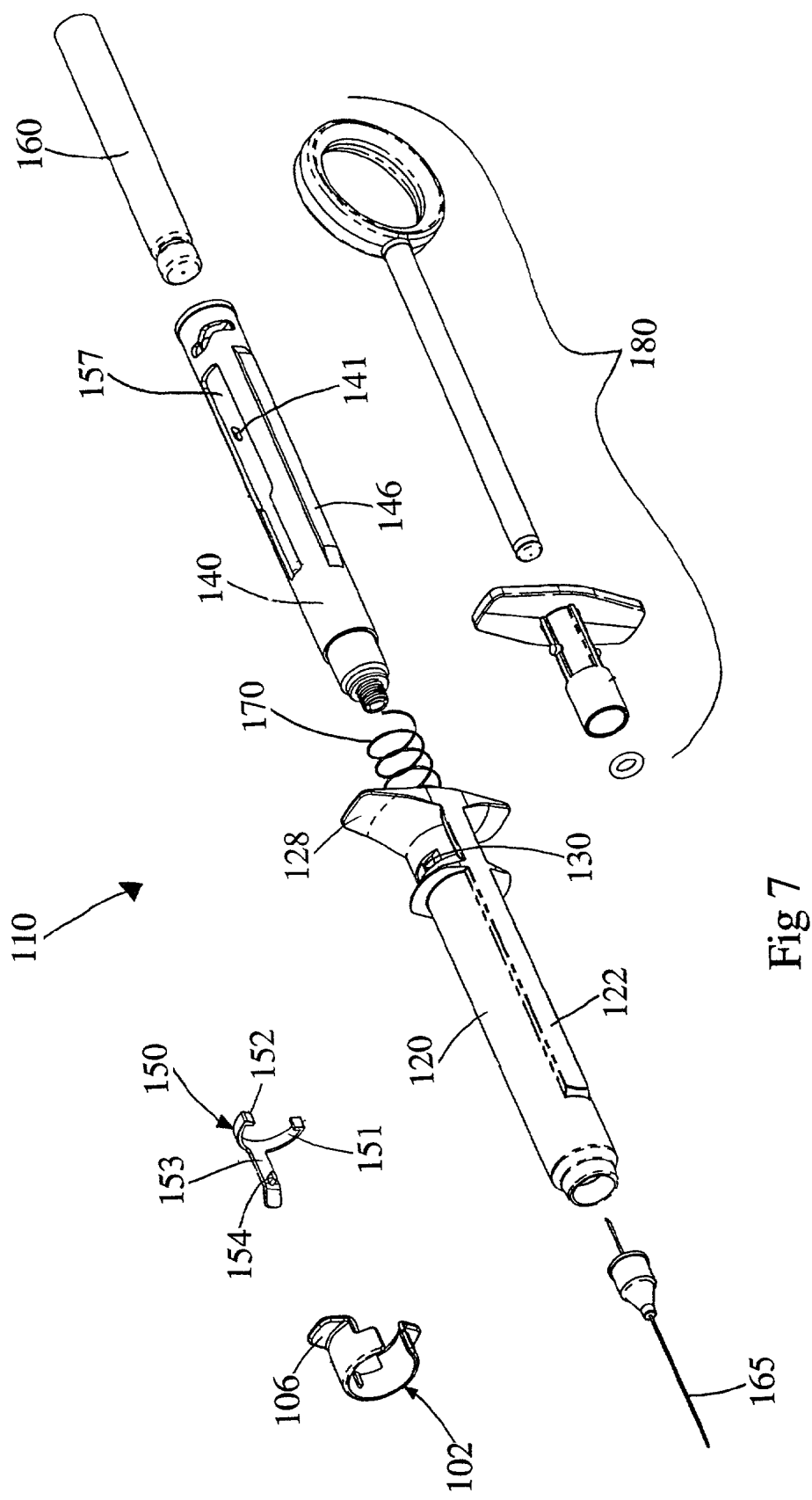
FIG. 7 is an exploded perspective view of an alternate embodiment of a retractable needle medical device.

Referring to FIG. 7, a pair of lateral slots 130 are formed in the wall of the barrel 120 transverse the longitudinal axis of the barrel. Preferably, the slots 130 are formed approximately 180 degrees apart from one another to provide a top slot and a bottom slot through the wall of the barrel. When the clip 150 is attached to the barrel 120, the radial tabs 152 extend through the slots 130 and cooperate with the inner housing 140 to prevent the inner housing from being completely removed from the barrel 120. In particular, the inner housing 140 includes a pair of access windows 157 similar to the previous embodiment. The forward ends of the access windows 157 form shoulders that engage the tabs 152 on locking clip 150 which extend through the barrel 120. The engagement between the locking clip 150 and the forward end of the access windows 157 limits the rearward displacement of the inner housing 140 relative to the barrel 120. This prevents the inner housing from being completely removed from the rear end of the barrel, which would expose the contaminated needle 165.

The inner housing 140 is slidably displaceable in the barrel 120 and comprises a first locking aperture 141 toward the rearward end of the housing and a second locking aperture 142 toward the forward end of the housing. The locking apertures 141, 142 are axially aligned on the inner housing and are configured to cooperate with the clip 150. More specifically, locking aperture 141 cooperates with the locking tab 154 on the clip 150 to releasably lock the inner housing in a forward locked position, and locking aperture 142 cooperates with the radial tab on the clip to releasably lock the inner housing in a rearward locked position. The inner housing 140 further includes an alignment rib 146 configured to slidably engage an interior channel 122 in the barrel 120 to prevent rotation of the inner housing as it is axially displaced within the barrel.

Referring now to FIGS. 7–9, the cooperation between the clip 150 and locking apertures 141,142 will be described in greater detail. The cantilever beam 153 on the clip 150 includes an inclined or ramped section 155 that extends radially outwardly from the barrel 120 when the clip is attached to the barrel. The ramped section 155 is configured to cooperate with a release sleeve 102 to actuate retraction of the needle 165 to the rearward locked position and facilitate forward displacement of the needle to the forward locked position. In particular, the release sleeve 102 is slidably disposed around the exterior of the barrel 120 and includes a ramped boss 104 that cooperates with the inclined section 155 on the cantilever beam 153. A pair of finger tabs 106 are disposed on the release sleeve 102 and are operable by a user's fingers to displace the sleeve rearwardly into engagement with the clip 150.

The components which control the displacement of the inner housing 140 between the forward locked position and rearward locked position are primarily disposed on the exterior of the device, as shown in FIGS. 7–9. Since the device 110 does not utilize an internal latch on the inner housing 140, locking windows are not required through the wall of the barrel 120. In addition, the inner housing does not require any cut-outs to accommodate inward deflection of a latch.

Figure 10:
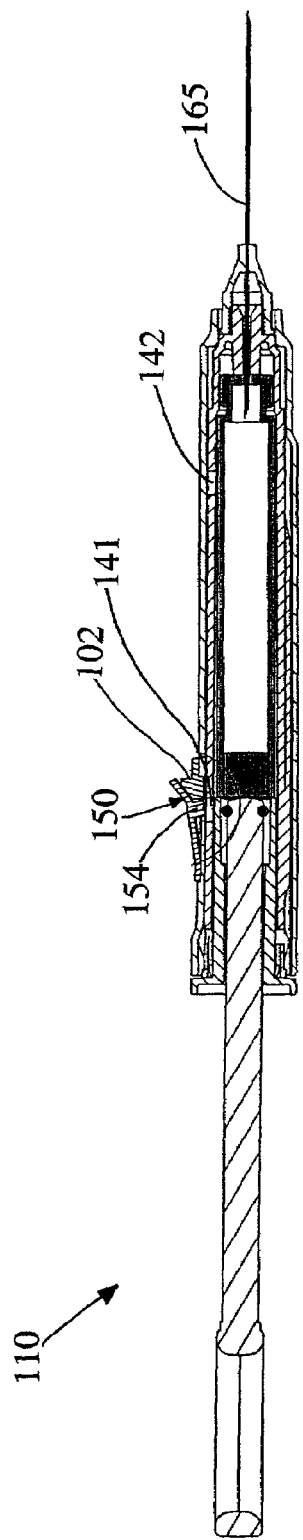
FIG. 10 is a cross-sectional view of the medical device illustrated in FIG. 7, illustrating the device after actuating retraction.

Operation of the device 110 will now be described. In general, the cartridge components are assembled and used to administer an injection in the same way as the previous embodiment. At the end of an injection, the needle 165 is retracted using the same hand that supports the device. In particular, the user moves one finger from the finger grip 128 on the barrel 120 and places the finger on one of the tabs 106 on the release sleeve 102. Alternatively, the user may keep fingers on the finger grips 128 and place a free finger on the release sleeve 102. To retract the needle, the release sleeve 102 is axially displaced rearwardly on the barrel into engagement with the inclined section 155 of the cantilever beam 153. The inclined section 155 rides along the top of the ramped boss 104 and gradually deflects upwardly, as shown in FIG. 10. As the inclined section is deflected upwardly by the ramped boss 104, the radial tab 154 is displaced radially outwardly and out of engagement with the first locking aperture 141. The inner housing 140 is no longer retained in the forward locked position against the bias of the spring 170 by the radial tab 154.

As in the previous embodiment, the needle 165 will not retract until the user releases the plunger, which retracts and moves with the needle. Therefore, the user releases pressure on the plunger 180 to allow the inner housing 140 and needle 165 to be retracted rearwardly by the spring. The release sleeve 102 is maintained in engagement with the clip 150 as pressure is removed from the plunger in order to retract the needle 165. Otherwise, the radial tab 154 may re-engage with the first locking aperture on the inner housing 140 as the plunger is released, and no retraction will occur.

As the inner housing 140 is retracted rearwardly by the spring, the radial tab 154 on cantilever beam 153 rides along the exterior of the inner housing 140 in an outwardly deflected position. The tab 154 remains deflected outwardly until the second locking aperture 142 on the inner housing 140 aligns with the tab. During retraction, the alignment rib 146 rides within the channel 122 in the barrel 120, maintaining the alignment between the tab 154 and the locking apertures 141, 142. When the second locking aperture 142 aligns with the tab 154, the cantilever beam 153 resiliently deflects inwardly so that the tab engages the second locking aperture, as shown in FIG. 11. In this position, the contaminated tip of the needle is shielded within the barrel 120.

Further injections can be administered by again pulling back the release sleeve 150 and re-extending the needle 165 to the forward locked position. Re-extension of the needle 165 from the rearward locked position to the forward locked position can be performed with the one hand that supports the device. The user places a finger on a tab 106 on the release sleeve 102 and pulls the sleeve rearwardly into engagement with the inclined section 155 of the cantilever beam 153. The inclined section 155 rides along the top of the ramped boss 104 and gradually deflects upwardly. As the inclined section is deflected upwardly by the ramped boss 104, the radial tab 154 is displaced radially outwardly and out of engagement with the second locking aperture 141. The inner housing 140 is no longer retained in the rearward locked position by the radial tab 154.

To re-extend the needle, axial pressure is applied to the plunger 180 assembly to advance the inner housing 140 and needle 165 forwardly through the barrel 120. As the inner housing 140 is advanced forwardly, the radial tab 154 on cantilever beam 153 rides along the exterior of the inner housing 140 in an outwardly deflected position. The tab 154 remains deflected outwardly until the first locking aperture 141 on the inner housing 140 aligns with the tab. When the first locking aperture 141 is aligned with the tab 154, the cantilever beam 153 resiliently deflects inwardly so that the tab engages the first locking aperture, as shown in FIG. 9. The needle 165 is again locked in the forward locked position to administer another injection. The release sleeve 150 may be engaged with the clip 150 repeatedly to retract and advance the needle for an unlimited number of injections.

Referring now to FIGS. 12–15, a third embodiment of the present invention is shown and designated 210. The device 210 features a one-piece releasable lock 250 that is operable to allow retraction and re-extension of a needle 265 so that the needle can be used for multiple injections. As in the second embodiment, the device 210 includes a needle 265 for piercing a patient, an inner housing 240, a barrel 220 and a plunger assembly 280 for ejecting medication from a pre-filled cartridge 260 into a patient. The inner housing 240 is slidably displaceable within the barrel 220 between a forward locked position, in which the needle 265 projects forwardly from the barrel 220, and a rearward locked position, in which the needle tip is shielded within the barrel.

The inner housing 240 includes an alignment rib 246 configured to slidably engage an interior channel 222 in the barrel 220 to prevent rotation of the inner housing as it is axially displaced within the barrel. A compression spring 270 is disposed between the barrel 220 and the inner housing 240 to bias the inner housing rearwardly toward the rearward locked position. The barrel 220 includes a pair of opposing finger grips 228 projecting radially outwardly from the rearward end of the barrel. The finger grips 228 provide a manual surface for grasping the barrel during use.

Figure 12:
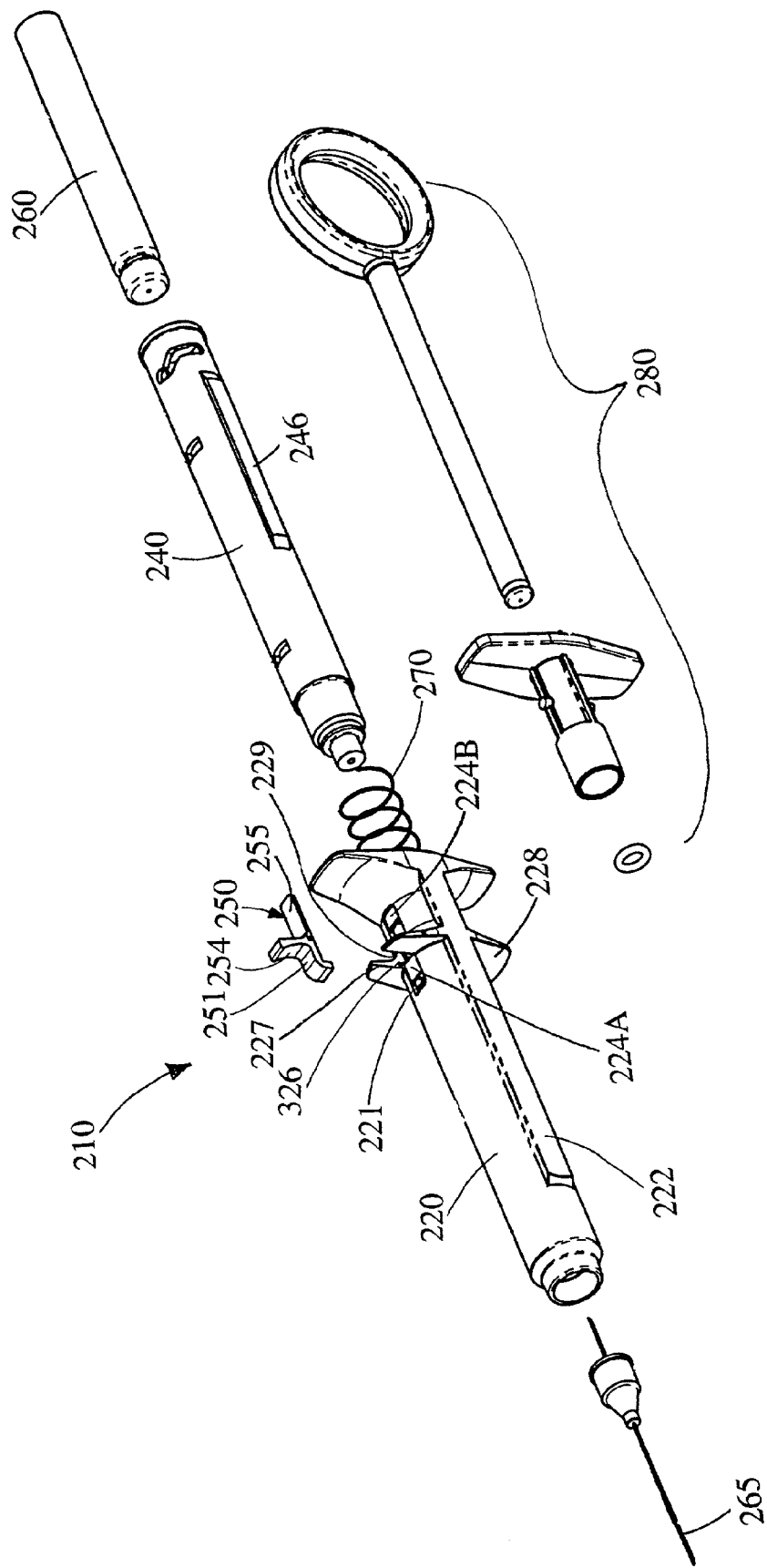
FIG. 12 is an exploded perspective view of a third embodiment of a retractable needle medical device.

Referring now to FIGS. 12–13C, the releasable lock 250 generally includes an elongated resiliently flexible lever 251 pivotally mounted in an opening 221 in the wall of the barrel 220. The lever 251 is mounted on a pivot axle 322 formed within the elongated opening 221. The pivot axle 322 is oriented in a direction perpendicular to the longitudinal axis of the barrel 220 and extends through a bore 223 extending through a medial portion of the lever 251. The lever 251 has a detent 253 at the forward end of the lever that projects radially inwardly through the opening 221 and into the interior of the barrel 220. The detent 253 is configured to releasably engage a pair of locking apertures on the inner housing 240. In particular, the detent 253 is configured to extend through a first locking aperture 241 to releasably retain the needle 265 and inner housing 240 in the forward locked position against the bias of the spring. The detent is also configured to extend through a second locking aperture 242 to releasably retain the needle 265 and inner housing 240 in the rearward locked position.

Figure 15:
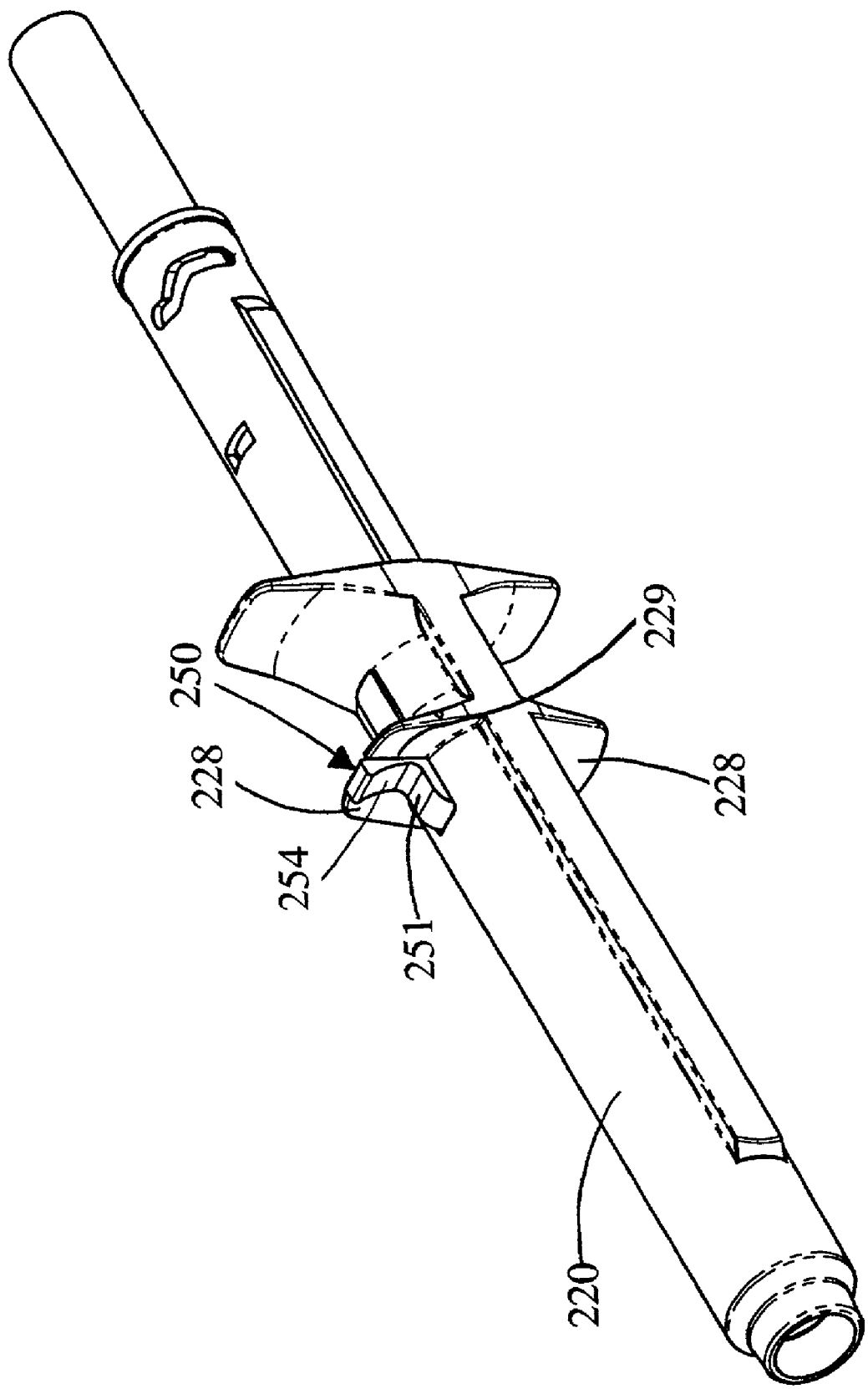
FIG. 15 is a fragmentary perspective view of the medical device illustrated in FIG. 13A, illustrating the device in a retracted position.

The releasable lock 250 is configured to pivot the detent 253 into and out of engagement with the locking apertures 241,242 on the inner housing 240. Referring now to FIGS. 12 and 15, the releasable lock 250 includes a flexible pull tab 254 that extends transversely from a medial portion of the lever 251 above the pivot axle 322. The lever 251 and pull tab 254 are disposed within a generally rectangular cut out 229 that bisects one of the finger grips 228 on the barrel 220. The cut out 229 forms a pair of opposing end walls 226 in the finger grip 228 that each contain a mounting hole 227. Each mounting hole 227 is adapted to receive an end of the pivot axle 222 so that the axle is mounted within the cutout. The axle 222 may be mounted in the cutout 229 using any method known in the art, such as press fit connections or by bonding the ends of the axle in the mounting holes 227. Preferably, the axle is formed using a material that permits a smooth low friction pivot connection with the lever 251.

Referring now to FIGS. 13B and 13C, the flexible pull tab 254 is operable to move the lever 251 between an engaged position, in which the detent 253 protrudes through the wall of the barrel 220, and a deflected position, in which the detent is deflected outwardly from the wall of the barrel. The engaged position is illustrated in FIG. 13B. The deflected position is illustrated in FIG. 13C. The pull tab 254 is operable to disengage the detent 253 from the locking apertures on the inner housing 240. The detent 253 is integrally connected to the medial portion of the lever 251 and pull tab 254. In this way, a rearward force applied to the pull tab 254 is transferred to the medial portion of the lever to impart a moment about the pivot axis. This moment is transferred to the forward end of the lever to cause the detent 253 to deflect radially outwardly with respect to the inner housing 240 and barrel 220.

The lever 251 is resiliently flexible to allow the detent 253 to deflect radially inwardly and back into engagement with the inner housing 240 when pressure is released from the pull tab 254. In particular, the lever 251 rests on a front platform 224A and rear platform 224B that are disposed within the elongated opening 221 in the wall of the barrel 220. A cantilever arm 255 extends rearwardly from the medial portion of the lever 251 and rests on the rear platform 224B. The engagement between the cantilever arm 255 and rear platform 224B prevents rotational displacement of the cantilever arm and counteracts the moment force so as to bias the lever 251 toward the engaged position.

Operation of the device 210 will now be described. In general, the cartridge components are assembled and used to administer an injection in the same way as the previous embodiment. At the end of an injection, the needle 265 is retracted using the same hand that supports the device. In particular, the user moves one finger from the finger grip 228 on the barrel 220 and places the finger on the pull tab 254 on the releasable lock 250. To retract the needle 265, the pull tab 254 is pulled rearwardly to rotate the lever 251 and displace the detent 253 out of engagement with the first locking aperture 241. The inner housing 240 is no longer retained in the forward locked position against the bias of the spring 270 by the detent 253.

As in the previous embodiment, the needle 265 will not retract until the user releases the plunger assembly 280, which retracts and moves with the needle. Therefore, the user releases pressure on the plunger assembly 280 to allow the inner housing 240 and needle 265 to be retracted rearwardly by the spring 270. The pull tab 254 is maintained in a pulled back position as pressure is removed from the plunger in order to retract the needle 265. Otherwise, the detent 253 may re-engage with the first locking aperture 241 on the inner housing 240 as the plunger assembly is released, and no retraction will occur.

Figure 14:
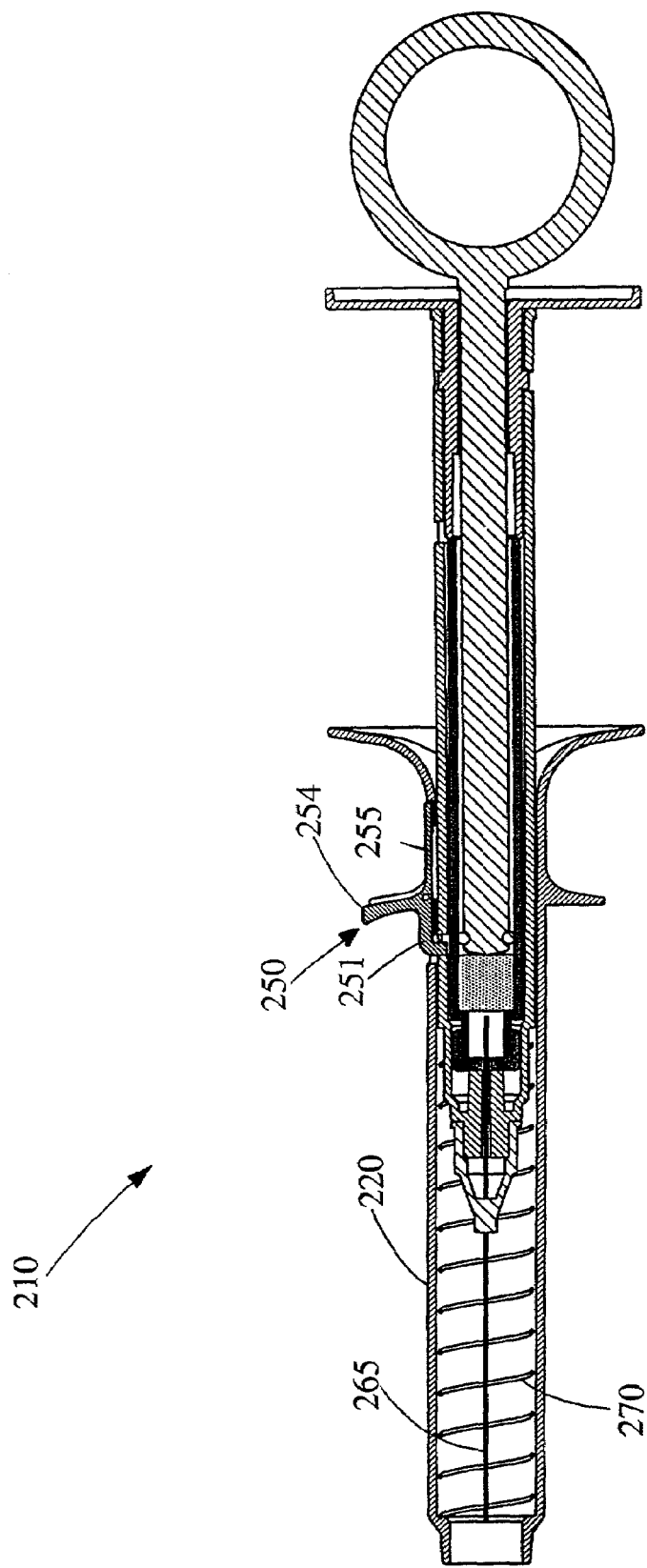
FIG. 14 is a cross-sectional view of the medical device illustrated in FIG. 13A, illustrating the device in a retracted position.

As the inner housing 240 is retracted rearwardly by the spring 270, the detent 253 on the lever 251 rides along the exterior of the inner housing 240 in the deflected position. The detent 253 remains deflected outwardly until the second locking aperture 242 on the inner housing 240 aligns with the detent. During retraction, the alignment rib 246 rides within the channel 222 in the barrel 220, maintaining the alignment between the detent 253 and the locking apertures 241,242. When the second locking aperture 242 aligns with the detent 253, the lever 251 resiliently deflects inwardly to the engaged position so that the detent engages the second locking aperture, as shown in FIG. 14 In this position, the contaminated tip of the needle 265 is shielded within the barrel 220.

Further injections can be administered by again pulling back the pull tab 254 and re-extending the needle 265 to the forward locked position. Re-extension of the needle 265 from the rearward locked position to the forward locked position can be performed with the one hand that supports the device. The user places a finger on the pull tab 254 and pulls the pull tab rearwardly. The lever 251 is rotated to the deflected position, and the detent 253 disengages from the second locking aperture 242. The inner housing 240 is no longer retained in the rearward locked position by the detent 253.

To re-extend the needle 265, axial pressure is applied to the plunger assembly 280 to advance the inner housing 240 and needle 265 forwardly through the barrel 220. As the inner housing 240 is advanced forwardly, the detent 253 rides along the exterior of the inner housing 240 in the deflected position. The detent 253 remains deflected outwardly until the first locking aperture 241 on the inner housing 240 aligns with the detent. When the first locking aperture 241 is aligned with the detent 253, the lever 251 resiliently deflects radially inwardly with respect to the barrel 220 so that the detent engages the first locking aperture, as shown in FIG. 13A. The needle 265 is again locked in the forward locked position to administer another injection. The releasable lock 250 may be engaged repeatedly to retract and advance the needle for an unlimited number of injections.

The terms and expressions which have been employed are used as terms of description and not of limitation. There is no intention in the use of such terms and expressions of excluding any equivalents of the features shown and described or portions thereof. It is recognized, however that various modifications are possible within the scope and spirit of the invention as set forth in the following claims.

The invention claimed is:

1. A medical device, comprising:
   a hollow barrel having an open rearward end;
   a cartridge containing a quantity of fluid;
   an inner housing slidably displaceable within the barrel, and having an opening for receiving the cartridge;
   a needle having a sharpened tip in fluid communication with the cartridge;
   an axially displaceable plunger operable to expel fluid from the cartridge;
   a connector for connecting the plunger to the inner housing;
   a first lock releasably retaining the needle in a projecting position in which the sharpened tip of the needle is exposed for use;
   a second lock releasably retaining the needle in a retracted position in which the sharpened tip of the needle is shielded against inadvertent contact;
   a biasing element biasing the needle rearwardly; and
   an actuator manually operable to release the first lock for rearward retraction of the needle into displacement with the second lock, and manually operable to release the second lock for forward displacement of the needle back into the first lock.

2. The medical device of claim 1 comprising a guide for impeding rotation of the housing relative to the barrel during retraction.

3. The medical device of claim 1 wherein the first lock comprises a first opening on the inner housing, and the second lock comprises a second opening on the inner housing and wherein the device comprises a radially deformable latch configured to cooperate with the first and second openings.

4. The medical device of claim 1 wherein the actuator comprises an axially displaceable sleeve circumscribing the barrel.

5. The medical device of claim 1 wherein displacing the inner housing rearwardly also displaces the plunger rearwardly.

6. The device of claim 1 wherein the actuator is disposed adjacent a rearward end of the barrel.

7. The device of claim 1 comprising a needle hub fixedly connected with the needle, wherein the needle hub comprises a first connector, and the inner housing comprises a second connector cooperable with the first connector to attach the needle hub to the inner housing.

8. The device of claim 1 wherein the cartridge comprises a seal and the plunger is operable to displace the seal within the cartridge.

9. The device of claim 1 wherein the biasing element biases the inner housing rearwardly.

10. The device of claim 1 wherein the plunger comprises a sleeve operable to drive the cartridge into engagement with the needle.

11. The device of claim 1 wherein the actuator is axially operable to actuate retraction.

12. A method for injecting medication from a medical device having a needle with a sharpened tip and an axially displaceable actuator, comprising the steps of:
providing a medical device having a barrel, inner housing displaceable within the barrel, and a needle;
inserting a cartridge of medicinal fluid into the inner housing;
connecting a plunger to the inner housing;
piercing a patient with the needle;
injecting fluid into the patient;
displacing an actuator to retract the needle so that the sharpened tip is shielded against inadvertent contact;
releasably locking the needle in the retracted position;
displacing the actuator to re-extend the needle so that the sharpened tip is exposed;
piercing the patient a second time with the needle; and
retracting the needle a second time so that the sharpened tip is shielded against inadvertent contact.

13. The method of claim 12 comprising the step of providing a biasing element for displacing the needle rearwardly during retraction of the needle.

14. The method of claim 12 comprising the step of providing a lock for releasably retaining the needle in a projecting position in which the sharpened tip of the needle is exposed for use.

15. A medical device for injecting medicinal fluid from a pre-filled container, comprising:
a barrel;
a needle having a sharpened tip operable between a projecting position in which the sharpened tip projects forwardly from the housing and a shielded position in which the sharpened tip is shielded;
a biasing element biasing the needle toward the shielded position;
a socket configured to receive the pre-filled container;
a needle retainer releasably retaining the needle against the bias of the biasing element;
a finger flange extending radially outwardly from the barrel to provide a gripping surface during use of the device;
a plunger adapted to expel medicinal fluid from the cartridge during use, wherein the plunger comprises a gripping surface adapted to be grasped in combination with the finger flange to drive the plunger forwardly; and
an actuator adapted to cooperate with the needle retainer to release the needle for retraction, wherein the actuator comprises a gripping surface disposed adjacent the finger flange gripping surface and generally parallel to the finger flange gripping surface to facilitate actuation of retraction by one-hand.

16. The device of claim 15 wherein the actuator gripping surface is configured to cooperate with the finger flange, such that the actuator can be actuated by one hand by releasing the plunger and squeezing the finger flange and actuator together.

17. The device of claim 16 wherein the actuator is a collar disposed around at least a portion of the barrel and the actuator is axially displaceable.

18. The device of claim 16 comprising a lock for locking the needle in the shielded position.

19. The device of claim 16 wherein the actuator is configured to cooperate with the needle retainer to displace the needle from the shielded position to the exposed position by squeezing the finger flange and the actuator together.

20. The device of claim 15 wherein the needle retainer comprises a radially deformable arm.

21. The device of claim 15 wherein the device is operable to displace the needle from the shielded position to the exposed position by pushing on the finger flange to displace the finger flange axially forwardly relative to the barrel.

22. A medical device, comprising:
a hollow barrel having an open rearward end;
a cartridge containing a quantity of fluid;
an inner housing slidably displaceable within the barrel, and having an opening for receiving the cartridge;
a needle having a sharpened tip in fluid communication with the cartridge;
a plunger operable to expel fluid from the cartridge;
a first lock comprising a first opening in one of either the barrel or the inner housing, releasably retaining the needle in a projecting position in which the sharpened tip of the needle is exposed for use;
a second lock comprising a second opening in the one of the barrel or the inner housing, releasably retaining the needle in a retracted position in which the sharpened tip of the needle is shielded against inadvertent contact;
a biasing element biasing the needle rearwardly; and
an actuator manually operable to release the needle from the first lock for rearward retraction of the needle into engagement with the second lock, and manually operable to release the needle from the second lock for forward displacement of the needle back into engagement with the first lock.

23. The device of claim 22 comprising a connector for connecting the plunger to the inner housing.

24. The medical device of claim 22 comprising a guide for impeding rotation of the housing relative to the barrel during retraction.

25. The medical device of claim 22 wherein the actuator comprises an axially displaceable sleeve circumscribing the barrel.

26. The medical device of claim 22 wherein displacing the inner housing rearwardly also displaces the plunger rearwardly.

27. The medical device of claim 22 comprising:
a finger flange extending radially outwardly from the barrel to provide a gripping surface during use of the device;
wherein the plunger comprises a gripping surface adapted to be grasped in combination with the finger flange to drive the plunger forwardly; and
wherein the actuator comprises a gripping surface disposed adjacent the finger flange gripping surface and generally parallel to the finger flange gripping surface to facilitate actuation of retraction by one-hand.

28. The device of claim 22 comprising a radially displaceable latch cooperable with the first lock and the second lock, wherein the latch is cooperable with the first lock to retain the needle in the extended position and the latch is cooperable with the second lock to retain the needle in the retracted position.

* * * * *